US006759216B1

(12) United States Patent
Lollar

(10) Patent No.: US 6,759,216 B1
(45) Date of Patent: Jul. 6, 2004

(54) GLYCOSYLATED, LOW ANTIGENICITY LOW IMMUNOGENICITY FACTOR VIII

(75) Inventor: John S. Lollar, Decatur, GA (US)

(73) Assignee: Emory University, Atlanta, GA (US)

( * ) Notice: Subject to any disclaimer, the term of this patent is extended or adjusted under 35 U.S.C. 154(b) by 0 days.

(21) Appl. No.: 09/435,403

(22) Filed: Nov. 5, 1999

Related U.S. Application Data

(60) Provisional application No. 60/107,402, filed on Nov. 6, 1998.

(51) Int. Cl.$^7$ .......................... C12N 15/00; C07K 1/00; C07K 14/00
(52) U.S. Cl. ..................... 435/69.6; 435/69.1; 530/350; 530/380; 530/383; 536/23.1; 930/10; 930/100
(58) Field of Search ........................ 536/23.1; 530/350, 530/380, 383, 829; 435/69.1, 69.6, 7.6, 440; 930/10, 100; 514/2

(56) References Cited

U.S. PATENT DOCUMENTS

| | | | | |
|---|---|---|---|---|
| 5,041,376 A | * | 8/1991 | Gething et al. | .......... 435/172.3 |
| 5,585,250 A | * | 12/1996 | Garrity et al. | ............. 435/69.3 |
| 5,859,204 A | | 1/1999 | Lollar | ........................ 530/383 |

OTHER PUBLICATIONS

Aly et al. Hemophilia A due to mutations that create new N–glycosylation sites. Jun. 1992, Proc. Natl. Acad. Sci., USA, vol. 89, pp. 4933–4937.*
Aledort, L., "Inhibitors in hemophilia Patients: Curent Status and Management"; (1994) *Am. J. Hematol.* (Review) 47:208–217.
Eaton, D.L. et al., "Construction and Characterization of an Active Factor VIII Variant Lacking the Central One–Third of the Molecule"; (1986) *Biochemistry* 25:8343–8347.
Fulcher, C.A. et al., "Localization of human factor FVIII inhibitor epitopes to two polypeptide fragments"; (1985) *Proc. Natl. Acad. Sci. USA* 82:7728–7732.
Healey, J.F. et al., "Residues 484–508 Contain a Major Determinant of the Inhibitory Epitope in the A2 Domain of Human Factor VIII"; (1995) *J. Biol. Chem.* 270:14505–14509.
Healey, J.F. et al., "Residues Glu2181–Val2243 Contain a Major Determinant of the Inhibitory Epitope in the C2 Domain of Human Factor VIII"; (1998) *Blood* 92:3701–3709.
Kasper, C.K. et al., "A More Uniform Measurement of Factor VIII Inhibitors"; (1975) *Thromb. Diath. Haemorr.* 34:869–872.

Lubin, I.M. et al., "Elimination of a Major Inhibitor Epitope in Factor VIII"; (1994) *J. Biol. Chem.* 269:8639–8641.
Lubin, I.M. et al., "Analysis of the human factor VIII A2 inhibitor epitope by alanine scanning mutagenesis"; (1997) *J. Biol. Chem.* 272:30191–30195.
Lusher, J.M. et al., "Recombinant Factor VIII for the Treatment of Previously Untreated Patients with Hemophilia A"; (1993) *N. Engl. J. Med.* 328:453–459.
McMillan, C.M. et al., "The Natural History of Factor VIII:C Inhibitors in Patients With Hemophilia A: A National Cooperative Study. II. Observations on the Initial Development of Factor VIII:C Inhibitors"; (1988) *Blood* 71:344–348.
Scandella, D. et al., "Epitope mapping of human factor VIII inihibitor antibodies by deletion analysis of factor VIII fragments expressed in *Eschericha coli*"; (1988) *Proc. Natl. Acad. Sci. USA* 85:6152–6156.
Scandella, D. et al., "A Recombinant Factor VIII A2 Domain Polypeptide Quantitatively Neutralizes Human Inhibitor Antibodies That Bind to A2"; (1993) *Blood* 82:1767–1775.
Vehar, G.A. et al., "Structure of human factor VIII"; (1984) *Nature* 312:337–3.
Wyatt, R. et al., "The antigenic structure of the HIV gp120 envelope glycoprotein"; (1998) *Nature* 393:705–711.

* cited by examiner

*Primary Examiner*—Christopher S. F. Low
*Assistant Examiner*—Holly Schnizer
(74) *Attorney, Agent, or Firm*—Greenlee, Winner and Sullivan, P.C.

(57) ABSTRACT

The development of inhibitory antibodies to blood coagulation factor VIII (fVIII) results in a severe bleeding tendency. These antibodies arise in patients with hemophilia A (hereditary fVIII deficiency) who have been transfused with fVIII. They also occur in non-hemophiliacs, which produces the condition acquired hemophilia. We describe a method to construct and express novel recombinant fVIII molecules which escape detection by existing inhibitory antibodies (low antigenicity fVIII) and which decrease the likelihood of developing inhibitory antibodies (low immunogenicity fVIII).

In this method, fVIII is glycosylated at sites that are known to be antibody recognition sequences (epitopes). This produces the desired properties of low antigenicity fVIII and low (immunogenicity fVIII. The mechanism is similar to one used by viruses such as the AIDS virus, which glycosylates its surface proteins to escape detection by the immune system.

1 Claim, No Drawings

SEQUENCE LISTING

<160> NUMBER OF SEQ ID NOS: 2

<210> SEQ ID NO 1
<211> LENGTH: 75
<212> TYPE: DNA
<213> ORGANISM: Homo sapiens

<400> SEQUENCE: 1
cgtcctttgt attcaaggag attaccaaaa ggtgtaaaac atttgaagga ttttccaaat     60
ctgccaggag aaata                                                     75

<210> SEQ ID NO 2
<211> LENGTH: 25
<212> TYPE: PRT
<213> ORGANISM: Homo sapiens

<400> SEQUENCE: 2

Arg Pro Leu Tyr Ser Arg Arg Leu Pro Lys Gly Val Lys His Leu Lys
 1               5                  10                  15

Asp Phe Pro Ile Leu Pro Gly Glu Ile
            20                  25

GLYCOSYLATED, LOW ANTIGENICITY LOW IMMUNOGENICITY FACTOR VIII

CROSS REFERENCE TO RELATED APPLICATIONS

This application claims priority from U.S. Provisional Patent Application No. 60/107,402, filed Nov. 6, 1998.

BACKGROUND OF THE INVENTION

Hemophilia A is defined as hereditary deficiency of blood coagulation fVIII. FVIII is synthesized as a ≈300 kDa single chain protein with internal sequence homology that defines the "domain" sequence $NH_2$-A1-A2-B-A3-C1-C2-COOH (FIG. 1) <{{33}}>. Domains are commonly delineated as A1 (Ala1-Arg372), A2 (Ser373-Arg740), B (Ser741-Arg1648), and A3-C1-C2 (Ser1690-Tyr2332) <{{398}}>. Despite its large size, the B domain of fVIII has no known function and can be deleted <{{11}}>. FVIII is measured by its ability to correct the prolonged clotting time of plasma prepared from patients with hemophilia A.

Hemophilia A is defined as hereditary deficiency of blood coagulation fVIII. fVIII is synthesized as a ≈300 kDa single chain protein with internal sequence homology that defines the "domain" sequence $NH_2$-A1-A2-B-A3-C1-C2-COOH (FIG. 1). Domains are commonly delineated as A1 (Ala1-Arg372), A2 (Ser373-Arg740), B (Ser741-Arg1648), and A3-C1-C2 (Ser1690-Tyr2332). Despite its large size, the B domain of fVIII has no known function and can be deleted. fVIII is measured by its ability to correct the prolonged clotting time of plasma prepared from patients with hemophilia A.

The development of inhibitory antibodies (inhibitors) to fVIII is a serious complication in the management of patients with hemophilia A. Alloantibodies develop in approximately 25% of patients with hemophilia A in response to therapeutic infusions of fVIII. In previously untreated patients with hemophilia A who develop inhibitors, the inhibitor usually develops within one year of treatment, although it can occur at any time. Additionally, autoantibodies that inactivate fVIII can occur in non-hemophiliacs in a variety of clinical settings including the postpartum period, in systemic lupus erythematosus, in chronic lymphocytic leukemia, and in elderly females. This condition is called acquired hemophilia.

fVIII inhibitors are measured clinically by the ability of the patient's plasma to inhibit fVIII in normal plasma. The standard test is the Bethesda assay. One Bethesda unit is defined as the dilution of patient plasma required to reduce the fVIII level by 50%.

A molecule is said to be antigenic when it binds to antibodies and immunogenic when it can induce an immune response. The immunogenicity of a molecule depends on the B cell repertoire, T cell help and suppression, and the major histocompatibility complex, which together determine the concentration and binding affinity of antibodies for an antigenic site. If a fVIII molecule could be constructed that did not bind to the inhibitory antibodies in a patient's plasma, it would useful therapeutically. Additionally, if a fVIII molecule could be constructed that is less immunogenic than wild-type human fVIII, i.e., could significantly lower the 25% incidence of inhibitor development, it would be safer than wild-type human fVIII. This molecule would have general applicability in the hemophilia A population.

Inhibitory antibodies to fVIII bind to either the A2, A3, or C2 domains of fVIII and disrupt specific functions associated with these domains. The A2 epitope is located within a linear sequence bounded by residues Arg484-Ile508. The C2 epitope has been localized to a sequence bounded by residues Glu2181-Val2243. The A3 epitope has not yet been mapped. The fact that fVIII epitopes are limited in number and can be mapped to the amino acid sequence level makes it possible to design strategies to produce low antigenicity and low immunogenicity fVIII molecules. We have already reduced the antigenicity of fVIII by replacing epitopes with non-human fVIII sequences and by site-directed mutagenesis of amino acids within fVIII epitopes.

Viruses, such as the human immunodeficiency virus (HIV), elude the immune system by varying epitopes that are recognized by antibodies. HIV contains an exterior envelope glycoprotein, gp120, which is targeted by the immune system in its attempts to rid the body of virus. HIV reduces the immunogenicity of gp120 using a post-translational process in which a polysaccharide is linked to asparagine residues. This process is called N-linked glycosylation because N is the single letter code for the amino acid asparagine. When the immune system makes antibodies to the existing glycosylated epitope, HIV responds by mutation vary its N-linked glycosylation sites. This reduces the immunogenicity of the virus. Similarly, the immunogenicity of fVIII could be reduced by altering the epitope by glycosylation. Additionally, the structure recognized by existing antibodies would be altered, reducing the antigenicity of the molecule.

SUMMARY OF THE INVENTION

The fVIII cDNA is modified to code for amino acids within known, existing epitopes to produce a recognition sequence for glysosylation at asparagine residues. The consensus amino acid sequence for N-linked glycosylation is N-X-S/T, where N is asparagine, X is any amino acid, S/T stands for serine and threonine. Modification of the cDNA is accomplished by site-directed mutagenesis using standard methods. Thus, any three residue sequence in fVIII can be altered to N-X-S/T to produce the desired recognition site. Alternatively, a sequence containing a serine or threonine can be altered by mutating a single site to asparagine to produce the desired N-X-S/T sequence.

The fVIII cDNA is inserted into a mammalian expression vector, which then is stably integrated into the genome of a mammalian host cell in culture. FVIII is secreted into the cell culture medium and purified. It is tested for antigenicity by measuring whether it is inhibited by inhibitory antibodies to fVIII that are obtained from patients. It is tested for immunogenicity by infusing it into hemophilia A mice and determining whether inhibitory antibodies develop.

DETAILED DESCRIPTION OF THE INVENTION

As an example of the method used to create glycosylated, low antigenicity, low immunogenicity fVIII, we describe the introduction of a recognition site for N-linked glycosylation at leucine 486 within the A2 epitope. FVIII contains a serine at position 488 within the A2 epitope. The 486–488 sequence is leu-tyr-ser. Therefore, mutation of leucine to asparagine produces a sequence N-Y-S (using the single letter code), which is a recognition site for N-linked glycosylation.

This mutation was introduced by site-directed mutagenesis of the human B-domainless fVIII cDNA. The cDNA sequence corresponding to residues 484–508 is shown in the Table. The DNA sequence is SEQ ID NO: 1; the translated, unmodified amino acid sequence is SEQ ID NO: 2.

```
484       AAC
CGT CCT TTG TAT TCA AGG AGA TTA CCA AAA
R   P   L   Y   S   R   R   L   P   K

508
GGT GTA AAA CAT TTG AAG GAT TTT CCA AAT CTG CCA GGA GAA ATA
G   V   K   H   L   K   D   F   P   I   L   P   G   E   I
```

The nucleotide sequence TTG, coding for leucine, was changed to AAC, which codes for asparagine.

The fVIII mutant cDNA, contained in the mammalian expression vector ReNeo, was transfected into COS-7 monkey cells for initial characterization. It was then stably transfected into baby hamster kidney cells using geneticin selection as described previously. The transformed cells expressed active fVIII, in this instance, human B-domainless L486N factor VIII.

As a further example, an N-linked glycosylation site was introduced into the C2 epitope. DNA encoding glutamine 2189 was mutated to encode asparagine, generating an asparagine-isoleucine-threonine amino acid sequence which is a recognition site for glycosylation at amino acid residue 2189.

It will be understood by those skilled in the art that other such modifications can be made within any of the domains giving rise to inhibitory analogs to provide N-linked glycosylation sites. Further, a plurality of such sites can be combined in a single fVIII molecule, so as to render the molecule unreactive (or less active than wild-type) to inhibitory antibodies. FVIII molecules modified according to this invention are also expected to have reduced immunogenicity.

What is claimed is:

1. A method for preparing a biologically active factor VIII having modified glycosylation comprising the steps of mutating a desired segment of factor VIII DNA to encode -N-X-S/T, where N is asparagine, X is any amino acid, and S/T is serine or threonine by replacing the leucine at residue 3 of SEQ ID NO:2 of the A2 domain with asparagine, thereby providing mutated factor VIII DNA encoding a post-translational glycosylation site at the desired segment of the factor VIII protein, and expressing the mutated DNA in a host cell capable of post-translational glycosylation, whereby biologically active factor VIII having modified glycosylation is prepared.

* * * * *